US006977247B2

(12) United States Patent
Rubinfeld et al.

(10) Patent No.: US 6,977,247 B2
(45) Date of Patent: Dec. 20, 2005

(54) SEQUENTIAL THERAPY COMPRISING A 20(S)-CAMPTOTHECIN AND A PYRIMIDINE BASE ANALOG

(75) Inventors: Joseph Rubinfeld, Danville, CA (US); Karl L. Mettinger, Berkeley, CA (US); John Lyons, Moraga, CA (US); Lawrence A. Romel, Oakland, CA (US)

(73) Assignee: SuperGen, Inc., Dublin, CA (US)

( * ) Notice: Subject to any disclaimer, the term of this patent is extended or adjusted under 35 U.S.C. 154(b) by 257 days.

(21) Appl. No.: 10/081,974

(22) Filed: Feb. 21, 2002

(65) Prior Publication Data

US 2003/0158148 A1 Aug. 21, 2003

(51) Int. Cl.[7] .................... A01N 43/04; A01N 43/42; A61K 31/70; A61K 31/44
(52) U.S. Cl. .................... 514/50; 514/34; 514/49; 514/256; 514/283
(58) Field of Search ................ 514/50, 34, 283, 514/256

(56) References Cited

U.S. PATENT DOCUMENTS

| | | | |
|---|---|---|---|
| 5,225,404 A | 7/1993 | Giovannella et al. | 514/81 |
| 5,573,781 A | 11/1996 | Brown et al. | 424/484 |
| 5,786,344 A | 7/1998 | Ratain et al. | 514/100 |
| 6,166,029 A | 12/2000 | Giovanella et al. | |
| 6,191,119 B1 * | 2/2001 | Rubinfeld | 514/34 |
| 6,342,487 B1 | 1/2002 | Riou et al. | 514/80 |
| 6,403,569 B1 * | 6/2002 | Achterrath | 514/50 |

OTHER PUBLICATIONS

Bernacki et al., "In Vitro Antitumor Activity of 9-Nitro-Camptothecin as a Single Agent and in Combination with other Antitumor Drugs", Annals of the New York Academy of Sciences, vol. 922, pp. 293-297, 2000.*

Devita, V., et al., Cancer: Principles and Practice of Onocology, (1997) 5th Edition, pp. 335-337.

Lee, J.H. et al., Antitumor Activity of 7-[2-(N-Isopropylamino)ethyl]-(20S)-Campthothecin, CKD602, as a Potent DNA Topoisomerase I Inhibitor, *Arch Pharm Res.* (1998), vol., 21, No. 5, pp. 581-589.

Luzzio, M.J. et al., Synthesis And Antitumor Acitvity of Novel Water Soluble Derivatives of Camptothecin as Specific Inhibitors of Topoisomerase I, *Journal of Medicinal Chemistry* (1995), vol. 38, No. 3, pp. 395-401.

Wall, M.E. et al., Plant Antitumor Agents. 30.[1a,b] Synthesis And Structure Activity of Novel Camptothecin Analogs, *J Med. Chem* (1993) vol. 36, No. 18, pp. 2689-2700.

* cited by examiner

*Primary Examiner*—James O. Wilson
*Assistant Examiner*—Traviss C. McIntosh, III
(74) *Attorney, Agent, or Firm*—Shirley Chen; Wilson Sonsini Goodrich & Rosati

(57) ABSTRACT

A method is provided for treating a patient having a disease associated with undesirable or uncontrolled cell proliferation, the method comprising: administering to the patient a 20(S)-camptothecin for a period of time during which a pyrimidine base analog is not being administered to the patient; and administering a pyrimidine base analog to the patient.

10 Claims, No Drawings

SEQUENTIAL THERAPY COMPRISING A 20(S)-CAMPTOTHECIN AND A PYRIMIDINE BASE ANALOG

BACKGROUND

1. Field of the Invention

This invention relates to a method for treating disease using a 20(S)-camptothecin and a pyrimidine base analog, and more specifically a method for treating disease using a 20(S)-camptothecin and pyrimidine base analog in a sequential therapy.

2. Description of Related Art

A. 20(S)-Camptothecins

20(S)-camptothecin, a plant alkaloid, was found to have anticancer activity in the late 1950's. Wall, M. et al., *Plant anti-tumor agents. I. The isolation and structure of camptothecin, a novel alkaloidal leukemia and tumor inhibitor from Camptotheca acuminata*, J. Am. Chem. Soc. 88: 3888–3890, (1966); Monroe E. Wall et al., *Camptothecin: Discovery to Clinic*, 803 Annals of the New York Academy of Sciences 1 (1996). These documents, and all documents (articles, patents, etc.) cited to herein, are incorporated by reference into the specification as if reproduced fully below. The chemical formula of camptothecin was determined to be $C_{20}^- H_{16} N_2 O_4$. 20(S)-camptothecin itself is insoluble in water. However, during the sixties and seventies the sodium salt of 20(S)-camptothecin was derived from 20(S)-camptothecin through opening of the lactone ring using a mild base. Clinical trials were then conducted using this hydrosoluble, sodium salt derivative of 20(S)-camptothecin (20(S)-camptothecin Na+), which was administered intravenously. The studies were later abandoned because of the high toxicity and low potency of 20(S)-camptothecin $Na^+$. Gottlieb, J. A., et al., *Preliminary pharmacological and clinical evaluation of camptothecin sodium salt (NSC 100880)*, Cancer Chemother. Rep. 54:461–470 (1979); Muggia, F. M., et al., *Phase I clinical trials of weekly and daily treatment with camptothecin (NSC 100880): Correlation with clinical studies*, Cancer Chemother. Rep. 56:515–521 (1972); Gottlieb, J. A. et al., *Treatment of malignant melanoma with camptothecin (NSC 100880)*, Cancer Chemother. Rep. 56:103–105 (1972); and Moertel, C. G., et al., *Phase II study of camptothecin (NSC 100880) in the treatment of advanced gastrointestinal cancer*, Cancer Chemother Rep. 56:95–101 (1972).

Despite its potential, interest in 20(S)-camptothecin as a therapeutic remained at a low ebb until the mid-1980's. By that time, drug therapies were being evaluated for treating human cancer using human cancer xenograft lines. During these evaluations, human tumors are serially heterotransplanted into immunodeficient, so-called Anude@ mice, and the mice then tested for their responsiveness to a specific drug. (Giovanella, B. C., et al., *Cancer* 52(7): 1146 (1983)). The data obtained in these studies strongly support the validity of heterotransplanted human tumors into immunodeficient mammals, such as nude mice, as a predictive model for testing the effectiveness of anticancer agents.

20(S)-camptothecin, and later some of its substituted forms, elicited differential responses in the cell cycle of nontumorigenic and tumorigenic human cells in vitro. Although it is not yet understood why 20(S)-camptothecin and some of its substituted forms are cytostatic for nontumorigenic cells and cytotoxic for tumorigenic cells, the selective toxicity of the compounds against tumorigenic cells in vitro and in vivo was an especially interesting feature of these drugs.

Investigators began to experiment with various substituted forms of 20(S)-camptothecin. Good activity was found when various substitutions were made to the 20(S)-camptothecin scaffold. For example, 9-Amino-20(S)-Camptothecin (9AC) and 10, 2011-Methylendioxy-20(S)-Camptothecin (10, 2011 MD) are capable of having high anticancer activity against human colon cancer xenografts. Giovanella, B. C., et al., *Highly effective topoisomerase-1 targeted chemotherapy of human colon cancer in xenografts*, Science 246:1046–1048 (1989).

Additionally, 9-nitrocamptothecin (9NC) has shown high activity against human tumor xenograft models. 9NC has a nine position hydrogen substituted with a nitro moiety. 9NC has inhibited the growth of human tumor xenografts in immunodeficient nude mice and has induced regression of human tumors established as xenografts in nude mice with little or no appearance of any measurable toxicity. D. Chatterjee et al., *Induction of Apoptosis in Malignant and Camptothecin-resistant Human Cells*, 803 Annals of the New York Academy of Sciences 143 (1996).

U.S. Pat. No. 5,552,154 to Giovanella et al. disclosed methods of treating specific forms of cancer with water-insoluble 20(S)-camptothecin and derivatives thereof, having the closed-lactone ring intact. In particular, transdermal, oral and intramuscular methods of administration using solutions of water-insoluble 20(S)-camptothecin were disclosed.

Other substituted 20(S)-camptothecin compounds that have shown promise include 7-ethyl-10-hydroxy 20(S)-camptothecin, and other 7, 9, 10, 20 11-substituted compounds.

B. Pyrimidine Base Derivatives

Pyrimidine bases are a vital component of many currently used therapeutic products. Examples of commonly used pyrimidine based therapeutics include halogenated analogs of a pyrimidine base, particularly fluorinated analogs of a pyrimidine base, such as 5-fluorouracil and 5-flucytosine.

5-Fluorouracil was introduced as a rationally synthesised anti-cancer agent more than 30 years ago and is still widely used in the treatment of many cancers (Duschinsky, et al, J. Am. Chem. Soc., 79: 4559 (1957); Heidelberger, et al, Nature, 179: 663 (1957)). The utility of 5-fluorouracil has however been low due to toxic side effects, a common problem with anti-cancer agents.

A number of derivatives of 5-fluorouracil have been synthesised over the years, which are either active metabolites (Heidelberger, Cancer Research, 30: 1549 (1970); Burchenal, et al, Ann. NY. Acad. Sci, 255: 202 (1975); Saneyoshi, et al, Chem. Pharm. Bull., 26 (10): 2990 (1978)) or simple prodrugs which act as repository forms of 5-fluoruracil (Holshouser, et al, J. Med. Chem., 28: 242 (1985); Hiller, et al, Dokl. Akad. Nauk. USSR, 176: 332 (1967); Ueda, et al, Chem. Pharm. Bull., 30, (1): 125 (1982)). Some of these compounds provide less toxic alternatives to 5-fluorouracil and have found a place in clinical practice.

SUMMARY OF THE INVENTION

A method is provided for treating a patient having a disease associated with undesirable or uncontrolled cell proliferation, the method comprising: administering to the patient a 20(S)-camptothecin for a period of time during which a pyrimidine base analog is not being administered to the patient; and administering a pyrimidine base analog to the patient.

According to this method, the 20(S)-camptothecin is optionally administered at least 1, 2, 3, 4, 5, 10, 20 or more days before the pyrimidine base analog is administered. Also according to this method, the 20(S)-camptothecin is optionally administered between 1 and 90 days, 2 and 90 days, 3 and 90 days, 4 and 90 days, 5 and 90 days, 10 and 90 days or 20 and 90 days before the pyrimidine base analog is administered.

Also according to this method, the 20(S)-camptothecin is optionally administered at least 1, 2, 3, 4, 5, 10, 20 or more days after the pyrimidine base analog is administered. Also according to this method, the 20(S)-camptothecin is optionally administered between 1 and 90 days, 2 and 90 days, 3 and 90 days, 4 and 90 days, 5 and 90 days, 10 and 90 days or 20 and 90 days after the pyrimidine base analog is administered.

Also according to this method, the 20(S)-camptothecin is optionally administered between 1 and 90 days, 2 and 90 days, 3 and 90 days, 4 and 90 days, 5 and 90 days, 10 and 90 days or 20 and 90 days before and/or after the pyrimidine base analog is administered and is also administered within that period of time when the pyrimidine base analog is administered.

A method is also provided for treating a patient having a disease associated with undesirable or uncontrolled cell proliferation, the method comprising: administering to the patient a 20(S)-camptothecin for a period of time when a pharmacologically active pyrimidine base analog is not present in the patient's body; and administering a pyrimidine base analog to the patient.

According to this method, the 20(S)-camptothecin is optionally administered at least 1, 2, 3, 4, 5, 10, 20 or more days before the pharmacologically active pyrimidine base analog enters the patient's body. Also according to this method, the 20(S)-camptothecin is optionally administered between 1 and 90 days, 2 and 90 days, 3 and 90 days, 4 and 90 days, 5 and 90 days, 10 and 90 days or 20 and 90 days before the pharmacologically active pyrimidine base analog enters the patient's body.

Also according to this method, the 20(S)-camptothecin is optionally administered at least 1, 2, 3, 4, 5, 10, 20 or more days after the pharmacologically active pyrimidine base analog enters the patient's body. Also according to this method, the 20(S)-camptothecin is optionally administered between 1 and 90 days, 2 and 90 days, 3 and 90 days, 4 and 90 days, 5 and 90 days, 10 and 90 days or 20 and 90 days after the pharmacologically active pyrimidine base analog enters the patient's body.

Also according to this method, the 20(S)-camptothecin is optionally administered between 1 and 90 days, 2 and 90 days, 3 and 90 days, 4 and 90 days, 5 and 90 days, 10 and 90 days or 20 and 90 days before or after the pharmacologically active pyrimidine base analog enters the patient's body and is also administered when an active form of the pyrimidine base analog is present in the patient.

In regard to the methods of the present invention, in one variation, the pyrimidine base analog is a fluorinated analog of a pyrimidine base. For example, it may be a fluorinated analog of uracil. In one particular embodiment, the pyrimidine base analog is 5-fluorouracil.

In regard to the methods of the present invention, in one variation, the 20(S)-camptothecin is 9-nitro-20(S)-camptothecin.

In regard to the methods of the present invention, in one variation, the disease associated with undesirable or uncontrolled cell proliferation is cancer. Examples of cancers include, but are not limited to acute myelogenous leukemia, cholangiocarcinoma, chronic myelogenous leukemia, lymphoma, melanoma, multiple myeloma, osteosarcoma, gastric sarcoma, glioma, bladder, breast, cervical, colorectal, lung, ovarian, pancreatic, prostrate, or stomach cancer.

DETAILED DESCRIPTION OF THE INVENTION

The present invention relates to the sequential delivery of a 20(S)-camptothecin and a pyrimidine base analog where one therapeutic agent, most typically a 20(S)-camptothecin, is administered to a patient for a period of time during which the other therapeutic agent is not administered to the patient. Optionally, one therapeutic agent is administered to a patient when the other is not present in a pharmacologically active form in the patient's body. The period of time when only one of the therapeutic agents is administered or where only one of the therapeutic agents is present in a pharmacologically active form in the patient's body may be at least one, two, three, four, five or more days.

It is noted that sequential delivery optionally also includes periods of time where both therapeutic agents are administered to the patient and/or where both therapeutic agents are present in pharmacologically active forms in the patient's body.

By administering these different therapeutic agents to a patient for periods of time where one but not the other therapeutic is administered, it is believed that these therapeutic agents will be more therapeutically effective than if only one of the therapeutic agents is administered to the patient.

In some instances, diseased cells develop a tolerance for a given therapeutic agent over time. As a result, the efficacy of that therapeutic agent decreases. By sequentially administering a 20(S)-camptothecin such as 9-nitro-20(S)-camptothecin or a pyrimidine base analog such as 5-fluorouracil, some diseased cells are killed while other diseased cells are weakened but develop a resistance to the therapeutic agent. Then, by switching between the 20(S)-camptothecin and the pyrimidine base analog after administering one of them for a period of time, it is believed that the other therapeutic agent is better able to kill off the remaining diseased cells that had been weakened by the therapeutic agent that was first administered.

In one particular embodiment, the sequential method is employed for treating pancreatic cancer. Over 75% of pancreatic cancers carry mutants for the p53 gene. 5-Fluorouracil is not believed to have any activity in p53 mutant tumors. Thus, one would expect p53 mutant tumors to be refractory to 5-fluorouracil treatment. 9-Nitro-20(S)-camptothecin meanwhile depends solely on the presence of the topoisomerase enzyme and not on the p53 status of tumors. Given, the fact that both drugs are not directed toward the mutation most commonly associated with pancreatic cancer, the usefulness of these drugs with pancreatic cancer would not be predicted.

It is noted that 5-fluorouracil is highly toxic. The intensity of treatment with 5-fluorouracil is thus limited by its toxicity. 9-Nitro-20(S)-camptothecin meanwhile has a lower level of toxicity. By administering 9-nitro-20(S)-camptothecin during periods between administrations of 5-fluorouracil, the patient can be more aggressively and more effectively treated.

In one embodiment, sequential therapy is performed according to the present invention where a 20(S)-camptothecin such as 9-nitro-20(S)-camptothecin is administered at least a portion of time when a pyrimidine base analog such as 5-fluorouracil is not administered to the patient.

A portion of the time when the 20(S)-camptothecin is administered may optionally be when no pharmacologically active pyrimidine base analog such as 5-fluorouracil is present in the patient's body, for example in the patient's blood stream. It may be that a 20(S)-camptothecin is administered earlier than a pharmacologically active form of the pyrimidine base analog enters the patient's system. It also may be that a 20(S)-camptothecin is administered after the previously administrated pyrimidine base analog is processed by the patient's system. It also may be that a 20(S)-camptothecin is administered when only pharmacologically or therapeutically inactive forms of a pyrimidine base analog are present in patient's body.

The 20(S)-camptothecin is optionally administered at least one, two, three, four, five or more days before or after the administration of the pyrimidine base analog and/or the presence of the pyrimidine base analog in a pharmacologically active form in the patient's body.

In one variation, administration of a 20(S)-camptothecin includes administration before the pyrimidine base analog is administered. Administration of a 20(S)-camptothecin may also include administration after the pyrimidine base analog is administered. Optionally, a 20(S)-camptothecin is administered to the patient both before and after the pyrimidine base analog is administered. Optionally, a 20(S)-camptothecin is administered to the patient for a period of time before the pyrimidine base analog is administered, while the pyrimidine base analog is administered and for a period of time after the pyrimidine base analog is administered. It should be recognized that multiple cycles of administration may be performed where 20(S)-camptothecin is administered and then the pyrimidine base analog is administered, or where 20(S)-camptothecin is administered and the pyrimidine base analog is administered periodically administered during the time the 20(S)-camptothecin is administered.

In one variation, one or more repetitive cycles are performed comprising one or more doses of 20(S)-camptothecin and one or more doses of a pyrimidine base analog. As noted, cycles of administration of 20(S)-camptothecin and cycles of administration of pyrimidine base analog may overlap.

Optionally, a 20(S)-camptothecin is first administered to the patient until a physiological state is observed in the patient. Accordingly, the method may include administering the 20(S)-camptothecin and measuring one or more physiological states until a predetermined physiological state is reached, at which point administration of the 20(S)-camptothecin is discontinued. A pyrimidine base analog such as 5-fluorouracil may then be may be administered.

Alternatively or in addition, a pyrimidine base analog may first be administered to the patient until a physiological state is observed in the patient. Accordingly, the method may include administering the pyrimidine base analog and measuring one or more physiological states until a predetermined physiological state is reached, at which point administration of the pyrimidine base analog is discontinued. A 20(S)-camptothecin such as 9-nitro-20(S)-camptothecin may then be may be administered.

In regard to each of the above variations, the patient may optionally be taken off treatment with one agent for a period of time before receiving the other agent. For example, the period of time may be between one and thirty weeks, preferably between one and four weeks.

Optionally, the patient is treated sequentially with the 20(S)-camptothecin and the pyrimidine base analog in repeated iterations. More specifically, the patient may receive a 20(S)-camptothecin, then a pyrimidine base analog, then a 20(S)-camptothecin, then a pyrimidine base analog, etc.

Examples of particular physiological indicia for performing sequential treatment according to the present invention include, but are not limited to when the patient possesses one or more of the following: a point mutation in p53 in the tumor specimen were detected or, if p14 Arf might be expressed inappropriately or, if MDM-2 might be overexpressed above endogenous normal levels, or if MDM-2 showed aberrant phosphorylation levels due to hyperactive ras or growth factor pathways in the tumor.

One particular application of sequential treatments according to the present invention is their use in treating pancreatic cancer.

1. 20(S)-Camptothecin Compounds

As used herein, a 20(S)-camptothecin refers to any compound which comprises the general 20(S)-camptothecin scaffold. As such, 20(S)-camptothecin encompasses a wide range of substituted 20(S)-camptothecins including, 7, 9, 10, 20 11, 12-substituted compounds. Such substitutions may serve to provide differential activities over the unsubstituted camptothecin compound. Especially preferable are 9-nitro-camptothecin, 9-aminocamptothecin, 10, 2011-methylen-dioxy 20(S)-camptothecin, topotecan, irinotecan, 7-ethyl-10-hydroxy camptothecin, or another substituted camptothecin that is substituted at least one of the 7, 9, 10, 20 11, or 12 positions. Particular examples of substituted 20(S)-camptothecins include, but are not limited to, 9-nitro-20(S)-camptothecin, 9-amino-20(S)-camptothecin, 9-methyl-camptothecin, 9-chlorocamptothecin, 9-flouro-camptothecin, 7-ethyl camptothecin, 10-methylcamptothecin, 10-chloro-camptothecin, 10-bromo-camptothecin, 10fluoro-camptothecin, 9-methoxy-camptothecin, 11-fluoro-camptothecin, 7-ethyl-10-hydroxy camptothecin, 10, 2011-methylenedioxy camptothecin, and 10, 2011-ethylenedioxy camptothecin, and 7-(4-methylpiperazinomethylene)-10, 2011-methylenedioxy camptothecin.

It should be recognized that these camptothecins may optionally be further substituted. In one particular variation, the 20(S)-camptothecin is 9-nitro-20(S)-camptothecin.

2. Pyrmidine Based Analogs

A variety of pyrimidine base analogs may be used in sequential therapy with a 20(S)-camptothecin, particularly 9-nitro-20(S)-camptothecin and 9-amino-20(S)-camptothecin. In one variation, the pyrimidine base analog is a halogenated analog of a pyrimidine base, and more particularly a fluorinated analog of a pyrimidine base. In one variation, the pyrimidine base is uracil. In one particular variation, the pyrimidine base analog is 5-fluorouracil (5-fluoro-2,4(1H,3H)-pyrimidinedione).

3. Indications for Sequential Therapy

Preferable indications that may be treated using the sequential therapies of the present invention include those involving undesirable or uncontrolled cell proliferation. Such indications include restenosis, benign tumors, a various types of cancers such as primary tumors and tumor metastasis, abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants.

Specific types of restenotic lesions that can be treated using the present invention include coronary, carotid, and cerebral lesions. Specific types of benign tumors that can be treated using the present invention include hemangiomas, acoustic neuromas, neurofibroma, trachomas and pyogenic granulomas. Specific types of cancers that can be treated using this invention include acute myelogenous leukemia, bladder, breast, cervical, cholangiocarcinoma, chronic myelogenous leukemia, colorectal, gastric sarcoma, glioma, leukemia, lung, lymphoma, melanoma, multiple myeloma, osteosarcoma, ovarian, pancreatic, prostrate, stomach, or tumors at localized sites including inoperable tumors or in tumors where localized treatment of tumors would be beneficial, and solid tumors. In a more preferable embodiment, the types of cancer include pancreatic, and/or colorectal.

Treatment of cell proliferation due to insults to body tissue during surgery may be possible for a variety of surgical procedures, including joint surgery, bowel surgery, and cheloid scarring Diseases that produce fibrotic tissue include emphysema. Repetitive motion disorders that may be treated using the present invention include carpal tunnel syndrome. An example of cell proliferative disorders that may be treated using the invention is a bone tumor.

Abnormal angiogenesis that may be may be treated using this invention include those abnormal angiogenesis accompanying rheumatoid arthritis, psoriasis, diabetic retinopathy, and other ocular angiogenic diseases such as retinopathy of prematurity (retrolental fibroplastic), macular degeneration, corneal graft rejection, neuroscular glaucoma and Oster Webber syndrome.

The proliferative responses associated with organ transplantation that may be treated using this invention include those proliferative responses contributing to potential organ rejections or associated complications. Specifically, these proliferative responses may occur during transplantation of the heart, lung, liver, kidney, and other body organs or organ systems.

4. Delivery and Dosing of Therapeutic Agents

A wide variety of delivery methods and formulations may be used to separately deliver the 20(S)-camptothecin and the pyrimidine base analog. For example, each agent may be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The agents may optionally be administered in slow release dosage forms.

A variety of dosing regiments have been developed for 20(S)-camptothecins and pyrimidine base analogs, each depending on the particular indication and route of administration to be employed. Each therapeutic agent may be administered in any conventional dosage form.

Optionally, the following dosing ranges may be used per 50 kilogram body mass for a treatment or administration cycle of either a 20(S)-camptothecin: 10 to 4000 mg of the agent; 100 to 2000 mg; 200 to 1500 mg; or 500 to 1100 mg.

Provided herein are exemplary dosing schemes for different indications. It should be understood, however, that other dosing schemes may be employed without departing from the present invention.

A. 9-Nitro-20(S)-camptothecin

In one variation, 9-nitro-20(S)-camptothecin is administered orally. The dosing range suggested for this route of administration is typically between 0.3 $mg/m^2/day$/patient (minimum) and 3 $mg/m^2/day$/patient (maximum). For example, a preferred dose for patients with pancreatic cancer is 1.5 $mg/m^2/day$/patient. It is recommended to adjust the dose of 9-nitro-20(S)-camptothecin according to the patient's needs, preferring a higher dose when the overall response to the drug is positive, or preferring a lower dose when toxicity or progression of the disease is a problem.

9-Nitro-20(S)-camptothecin may be administered orally for two, three, four or five consecutive days followed by one or several days of rest. This cycle may be repeated two or more weeks. For example, for patients with pancreatic cancer, a 7-day schedule is preferred where 5 consecutive days of administration are followed by 2 days of rest. Because of the toxicity, the described cycle can be modified to shorten the number of days when 9-nitro-20(S)-camptothecin is administered. In some instances, it may be desirable to periodically discontinue 9-nitro-20(S)-camptothecin for one or more days, after which, administration is repeated.

In one example, a 8-week cycle of 9-nitro-20(S)-camptothecin administration is performed. If toxicity or progression of the disease is a major concern, the treatment can be discontinued at any time. If the patient demonstrates a positive response to the drug, the treatment may be prolonged for 90-weeks or longer.

In one particular example, patients with various types of cancer, including primary cancer and methastasis, receive orally 9-Nitro-20(S)-camptothecin. The dosage ranges between 1 and 2.5 $mg/m^2/day$ for 5 consecutive days followed by 2 days of rest. Dose escalations are permitted. Dose reductions are permitted when necessary and range as low as 0.6 $mg/m^2/day$ (5 days on, 2 days off). Patients are treated for as long as the overall response to the treatment is positive. The median number of weeks per patient is 11 (range 1 to 83 weeks). The dose limiting toxicity is hematological and gastrointestinal. The group of tumors that are known to regress after exposure to 9-Nitro-20(S)-camptothecin comprises of breast carcinoma, ovarian carcinoma, cholangiocarcinoma, monomyelocytic leukemia, and pancreatic carcinoma.

B. 5-Fluorouracil

In one variation, 5-fluorouracil is administered intravenously, typically as a 1%, 2%, or 5% solution. 5-fluorouracil is administered by injection and is commonly administered at 50 mg/ml.

In another variation, 5-fluorouracil is administered intravenously, typically as a 1%, 2%, or 5% solution.

In yet another variation, 5-fluorouracil is administered orally. For example, 5-fluorouracil is marketed for oral administration as a clear fluid Blue/orange capsules of 250 mg and 500 mg under the name UFTORAL. 5-fluorouracil.

In yet another variation, 5-fluorouracil is administered transdermally. For example, 5-fluorouracil is marketed as a 1% and 5% cream under the name EFUDEX.

5-fluorouracil may be administered two, three or four times daily for a period of two, three four or more weeks. Alternatively, a single, larger dose may be administered weekly. Because of its toxicity, it is common to periodically discontinue 5-fluorouracil for a week or so, after which, administration is repeated.

Folinic acid may be administered with 5-fluorouracil. Folic acid is believed to increase the effectiveness of 5-fluorouracil.

In one particular example, 5-fluorouracil is administered intravenously as follows. Initially, a 12 mg/kg/day dosage regiment for 4 days, not to exceed 800 mg/day. If no toxicity is seen, 6 mg/kg is administered on days 6, 8, 10, 20 and 12. The therapy is then discontinued on day 12 even if there are no toxic symptoms. For maintenance, the first course is repeated after a period of time or when toxicity from initial course of therapy is gone. In one variation, 10–15 mg/kg/ week is given as a single dose. Overall, it is recommended that the dosage should not exceed 1 g/week.

C. Exemplary Sequential Therapy Treatment Protocols

In this example, several different sequential therapy protocols are described involving 9-nitro-20(S)-camptothecin and 5-fluorouracil for patients with primary or metastatic carcinoma of the pancreas.

According to one treatment protocol, patients initially receive a 12 mg/kg/day dosage regiment of intravenously delivered 5-fluorouracil is applied for 4 days, not to exceed 800 mg/day. If no toxicity is seen, 6 mg/kg is administered on days 6, 8, 10, 20 and 12. The therapy is then discontinued on day 12 even if there are no toxic symptoms. Patients that demonstrate objective or symptomatic progression of pancreatic cancer after the competition of treatment with 5-fluorouracil receive 9-nitro-20(S)-camptothecin. The sequential stage begins at least 14 days after patients have received their final dose of 5-fluorouracil. The preferred dosage for oral administration of 9-nitro-20(S)-camptothecin is 1.5 mg/m$^2$/day. It is applied for 5 consecutive days followed by 2 days of rest. Dose escalations are permitted and range as high as 2 mg/m$^2$/day. The dose limiting toxicity is hematological and gastrointestinal. Dose reductions may be necessary to control toxicity and involve either reduction of dosage (up to 0.6 mg/m$^2$/day), or keeping the same dose level and shortening the schedule to four days of treatment per week, or shortening the overall course of 9-nitro-20(S)-camptothecin administration. Patients are treated with 9-nitro-20(S)-camptothecin for as long as the overall response to the treatment is positive. The preferred number of weeks is 11 with a typical range being between 1 to 83 weeks.

According to another treatment protocol, patients initially orally receive 9-nitro-20(S)-camptothecin. The preferred dosage is 1.5 mg/m$^2$/day applied for 5 consecutive days followed by 2 days of rest. In addition to 9-nitro-20(S)-camptothecin, patients receive an intravenous injection of 500 mg/day of 5-fluorouracil once per week. The intravenous injection is typically scheduled on the same day as one of the 9-nitro-20(S)-camptothecin administrations. Dose escalations are permitted and may range as high as 2 mg/m$^2$/day of 9-Nitro-20(S)-camptothecin, 800 mg/day of 5-fluorouracil. The dose limiting toxicity is hematological and gastrointestinal. Dose reductions may be necessary to control toxicity and involve either reduction of dosage (up to 0.6 mg/m$^2$/day for 9-nitro-20(S)-camptothecin, up to 4 mg/kg of 5-fluorouracil) or keeping the same dose level and shortening the schedule to four days of 9-nitro-20(S)-camptothecin treatment per week. The preferred length of the treatment is 8 weeks. Optionally, patients may be taken off treatment with 5-fluorouracil for one or more weeks.

According to another treatment protocol, the treatment comprises repetative cycles wherein patients are treated by 9-nitro-20(S)-camptothecin and 5-fluorouracil applied in a sequential manner. At the first stage, patients are scheduled to receive 9-nitro-20(S)-camptothecin for 5 consecutive days followed by 2 days of rest. The preferred dosage is 1.5 mg/m$^2$/day when applied orally. The dose limiting toxicity is hematological and gastrointestinal. Dose adjustments are permitted and range between 0.5 and 2 mg/m$^2$/day. The preferred length of this treatment is 8 weeks. At the second stage, patients receive 12 mg/kg/day of 5-fluorouracil (not to exceed 800 mg/day) for 4 consecutive days followed by 3 days of rest. Dose reductions may be necessary to control toxicity and involve either reduction of dosage (up to 4 mg/kg of 5-fluorouracil) or keeping the same dose level and shortening the schedule to 2 days of treatment followed by 5 days of rest. After the second stage is completed, the overall cycle can be repeated either immediately, or after a delay (2 weeks-long delay is preferred, range is 0 to 10). Patients are treated for as long as the overall response to the treatment is positive. The preferred number of cycles per patient is 2 (range 1 to 7 cycles).

It will be apparent to those skilled in the art that various modifications and variations can be made in the compounds, compositions, kits, and methods of the present invention without departing from the spirit or scope of the invention. Thus, it is intended that the present invention cover the modifications and variations of this invention provided they come within the scope of the appended claims and their equivalents.

What is claimed is:

1. A method for treating cancer in a patient, wherein the cancer has a p53 mutation, comprising:
   administering 5-fluorouracil to said patient; and
   administering to said patient 9-nitro-20(S)-camptothecin or 9-amino-20(S)-camptothecin at least 1 day after administering 5-fluorouracil to the patient and when 5-fluorouracil is not present in a pharmaceutically active form in said patient.

2. A method according to claim 1 wherein 9-nitro-20(S)-camptothecin or 9-amino-20(S)-camptothecin is administered at least 2 days after 5-fluorouracil is administered.

3. A method according to claim 1 wherein 9-nitro-20(S)-camptothecin or 9-amino-20(S)-camptothecin is administered at least 3 days after 5-fluorouracil is administered.

4. A method according to claim 1 wherein 9-nitro-20(S)-camptothecin or 9-amino-20(S)-camptothecin is administered at least 4 days after 5-fluorouracil is administered.

5. A method according to claim 1 wherein 9-nitro-20(S)-camptothecin or 9-amino-20(S)-camptothecin is administered at least 5 days after 5-fluorouracil is administered.

6. A method according to claim 1 wherein 9-nitro-20(S)-camptothecin or 9-amino-20(S)-camptothecin is administered between 2 and 90 days after 5-fluorouracil is administered.

7. A method according to claim 1 wherein 9-nitro-20(S)-camptothecin or 9-amino-20(S)-camptothecin is administered between 3 and 90 days after 5-fluorouracil is administered.

8. A method according to claim 1 wherein 9-nitro-20(S)-camptothecin or 9-amino-20(S)-camptothecin is administered between 4 and 90 days after 5-fluorouracil is administered.

9. A method according to claim 1 wherein said patient has pancreatic cancer.

10. A method according to claim 1 wherein said patient has cancer selected from the group consisting of acute myelogenous leukemia, cholangiocarcinoma, chronic myelogenous leukemia, lymphoma, melanoma, multiple myeloma, osteosarcoma, gastric sarcoma, glioma, bladder, breast, cervical, colorectal, lung, ovarian, pancreatic, prostate, and stomach caner.

* * * * *